(12) United States Patent
Anastassiou et al.

(10) Patent No.: US 8,086,409 B2
(45) Date of Patent: Dec. 27, 2011

(54) METHOD OF SELECTING GENES FROM CONTINUOUS GENE EXPRESSION DATA BASED ON SYNERGISTIC INTERACTIONS AMONG GENES

(75) Inventors: Dimitris Anastassiou, Tenafly, NJ (US); John Watkinson, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 845 days.

(21) Appl. No.: 12/022,862

(22) Filed: Jan. 30, 2008

(65) Prior Publication Data

US 2009/0012719 A1 Jan. 8, 2009

Related U.S. Application Data

(60) Provisional application No. 60/887,281, filed on Jan. 30, 2007.

(51) Int. Cl.
*G01N 33/48* (2006.01)
*C12Q 1/68* (2006.01)
*G06G 7/58* (2006.01)
(52) U.S. Cl. .................. 702/19; 702/20; 435/6; 703/11
(58) Field of Classification Search .................. None
See application file for complete search history.

(56) References Cited

U.S. PATENT DOCUMENTS

| | | |
|---|---|---|
| 6,996,476 B2 | 2/2006 | Najarian |
| 2003/0215866 A1 | 11/2003 | Liebovitch et al. |
| 2004/0241730 A1 | 12/2004 | Yakhini et al. |

FOREIGN PATENT DOCUMENTS

| | | |
|---|---|---|
| WO | WO2004/019264 | 4/2004 |
| WO | WO 2007/134167 | 11/2007 |

OTHER PUBLICATIONS

Boser, B.E., Guyon, I.M. & Vapnik, V.N.; A training algorithm for optimal margin classifiers, in 5th Annual Workshop con COLT, (ed. Haussler, D.) pp. 144-152, ACM Press 1992.
Eisen, M.B., Spellman, P.T., Brown, P.O. & Botstein, D.; Cluster analysis and display of genome-wide expression patterns; *Proc Natl Acad WSci USA* 95, pp. 14863-14868; 1998.
Mootha, V.K. et al.; PGC-1alpha-responsive genes involved in oxidative phosphorylation are coordinately downregulated in human diabetes; *Nat Genet* 34; pp. 267-273; 2003.
Rhodes, D.R. & Chinnaiyan, A.M.; Integrative analysis of the cancer transcriptome; *Nat Genetl; 37 Suppl*, pp. S31-S37; 2005.
Rhodes, D.R. et al.; Mining for regulatory programs in the cancer transcriptome; *Nat Genet* 37; pp. 579-583; 2005.
Segal, E., Friedman, N., Koller, D. & Regev A.; A module map showing conditional activity of expression modules in cancer; *Nat Genet* 36; pp. 1090-1098; 2004.
Subramanian, A. et al.; Gene set enrichment analysis: a knowledge-based approach for interpreting genome-wide expression profiles; *Proc Natl Aced Sci U S A.;* 103; pp. 15545-15550; 2005.
Tomlins, S.A. et al.; Integrative molecular concept modeling of prostate cancer progression; *Nat Genet* 39, pp. 41-51; 2007.
Cover, T.M. & Thomas, J.A.; *Elements of information theory*, xxiii, p. 748 (Wiley-Interscience; Hoboken, NJ); 2006.
Varadan, V. & Anastassiou, D.; Inference of disease-related molelcular logic from systems-based microarray analysis; *PLoS comput Biol* 2; pp. e681 2006.
Varadan, V., Miller, D.M., 3rd & Anastassiou, D.; Computational inference of the molecular logic for synaptic connectivity in C. elegans 22; pp. e497-506; 2006.
Singh, D. et al.; Gene expression correlates of clinical prostate cancer behavior; *Cancer Cel 1,* pp. 203-209; 2002.
Farias, E.F., Marzan, C. & Mira-y-Lopez, R.; Cellular retinol-binding protein-I inhibits PI3K/Akt signaling through a retinoic acid receptor-dependent mechanism that regulates p. 85-p. 110 heterodimerization; *Oncogene* 24; pp. 1598-1606; 2005.
Irizarry, R.A. et all; Exploration, normalization, and summaries of high density oligonucleotide array probe level data; *Biostatistics* 4, pp. 249-264; 2003.
U.S. Appl. No. 13/013,321, filed Jan. 25, 2011.
U.S. Appl. No. 12/307,694, filed May 4, 2009.
U.S. Appl. No. 12/133,045, filed Jun. 4, 2008.
U.S. Appl. No. 13/013,321, Feb. 1, 2011 Notice to File Corrected Application Papers.
U.S. Appl. No. 13/013,321, Mar. 1, 2011 Response to Notice to File Corrected Application Papers.
U.S. Appl. No. 12/307,694, Feb. 2, 2009 Petition under 37 CFR 1.137(b).
U.S. Appl. No. 12/307,694, Mar. 11, 2009 Missing Requirements.
U.S. Appl. No. 12/307,694, May 4, 2009 Response to Missing Requirements.
U.S. Appl. No. 12/133,045, Jun. 19, 2008 Missing Parts.
U.S. Appl. No. 12/133,045, Aug. 19, 2008 Response to Missing Parts.
U.S. Appl. No. 12/133,045, Nov. 15, 2010 Non-Final Office Action.
U.S. Appl. No. 12/133,045, Feb. 15, 2011 Response to Non-Final Office Action.
Bassett et al., "Gene Expression Informatics—It's All in Your Mine", Genetics Supplement, Jan. 1999, vol. 21, pp. 51-55. Bi et al., 2004, "Bipartite pattern discovery by entropy minimization-based multiple local alignment," *Nucleic Acids Research*, vol. 32, No. 17: p. 4979-4991.
Brazma et al., "Gene Expression Data Analysis" FEBS lett., Aug. 2000, vol. 480, pp. 17-24.
Furlanello et al., 2003, "Entropy-based gene ranking without selection bias for the predictive classification of microarray data," *BMC Bioinformatics*, 4:54.
Hamer et al., 2003 "Rational Design of Drugs That Induce Human Immunodeficiency Virus Replication," *Journal of Virology*, vol. 77, No. 19: p. 10227-10236.
Liu et al., 2005, "An Entropy-based gene selection method for cancer classification using microarray data," *BMC Bioinformatics*, 6:76.
International Search Report—Application No. PCT/US2006/061749 (Feb. 5, 2008).
International Search Report—Application No. PCT/US2007/06866 (Aug. 5, 2008).

*Primary Examiner* — Shubo Zhou
(74) *Attorney, Agent, or Firm* — Baker Botts L.L.P.

(57) ABSTRACT

Systems and methods for selecting factors from a continuous data set of measurements are provided. The measurements include values of factors and/or outcomes. Two or more factors that are jointly associated with one or more outcomes from the data set are identified. Each of the two or more factors are analyzed to determine at least one cooperative interaction among the factors with respect to an outcome. The two or more factors can be a module of factors serving as a single factor participating in a cooperative interaction with another factor or module of factors.

10 Claims, 3 Drawing Sheets

METHOD OF SELECTING GENES FROM CONTINUOUS GENE EXPRESSION DATA BASED ON SYNERGISTIC INTERACTIONS AMONG GENES

CROSS-REFERENCE TO RELATED APPLICATIONS

The present application claims priority to U.S. Provisional Application Ser. No. 60/887,281, filed Jan. 30, 2007, the entirety of the disclosure of which is explicitly incorporated by reference herein.

BACKGROUND

The disclosed subject matter relates generally to systems and methods for factor selection, including factors useful in gene expression analysis.

The expression levels of thousands of genes, measured simultaneously using DNA microarrays, can provide information useful for medical diagnosis and prognosis. However, gene expression measurements have not provided significant insight into the development of therapeutic approaches. This can be partly attributed to the fact that while traditional gene selection techniques typically produce a "list of genes" that are correlated with disease, they do not reflect interrelationships.

Gene selection techniques based on microarray analysis often involve individual gene ranking depending on a numerical score measuring the correlation of each gene with particular disease types. The expression levels of the highest-ranked genes tend to be either consistently higher in the presence of disease and lower in the absence of disease, or vice versa. Such genes usually have the property that their joint expression levels corresponding to diseased tissues and the joint expression levels corresponding to healthy tissues can be cleanly separated into two distinct clusters. These techniques are therefore convenient for classification purposes between disease and health, or between different disease types. However, they do not identify cooperative relationships or the synergy among multiple interacting genes.

There is therefore a need for the ability to analyze genes in terms of the cooperative, as opposed to independent, nature of their contributions towards a phenotype.

SUMMARY

The disclosed subject matter provides techniques for the analysis of the cooperative interactions or synergy among multiple interacting factors. The factors can be features, elements or outcomes that are cooperatively associated with one or more factors or outcomes by their joint presence or absence. The factors are selected from a data set of continuous measurements.

In some embodiments of the disclosed subject matter, methods for selecting factors from a data set of continuous measurements are provided. The measurements can include values of factors and/or outcomes. Two or more factors that are jointly associated with one or more outcomes from the data set are identified. Each of the two or more factors are analyzed to determine at least one cooperative interaction among the factors with respect to an outcome or factor. The factors can be a module of factors, where a module includes several factors acting as an individual factor, or a sub-module of factors. The interaction can be a structure of interactions, where a structure includes several interactions involving sub-modules of factors.

The factors can include two or more genes. The data set can include continuous gene expression data including expression levels for each of the genes. The outcomes include presence or absence of a disease, and the genes can be a module of genes, preferably a smallest cooperative module of genes with joint expression levels that can be used for a prediction of the presence of a disease.

In other embodiments of the disclosed subject matter, methods for selecting two or more genes from continuous gene expression data are provided. The continuous gene expression data can include expression levels for each of the two or more genes. The method includes providing continuous gene expression data for two or more genes, identifying two or more genes having high synergy, and identifying a cooperative interaction that connects the expression levels in the two or more genes with the presence or absence of a disease or trait.

The continuous gene expression data can be obtained from at least one microarray of gene expression analysis. The genes can be a module of genes. The cooperative interaction can be modeled using a Boolean function, a parsimonious Boolean function, or the most parsimonious Boolean function. The high synergy can be a maximum synergy.

In other embodiments of the disclosed subject matter, systems for selecting two or more genes from continuous gene expression data are provided. The continuous gene expression data includes expression levels for each of the two or more genes. The system includes at least one processor, a computer readable medium coupled to the processor including instructions which when executed cause the processor to provide gene expression data for the genes. The instructions also cause the processor to choose a single threshold for each of the two or more genes, identify the two or more genes with a high synergy, and identify the expression level of another third gene. The continuous gene expression data can be derived from a microarray of gene expression data. The two or more genes can be a module of genes. The high synergy can be a maximum synergy.

In other embodiments of the disclosed subject matter, systems for selecting factors from a data set of continuous measurements are provided. Each measurement can include values of the factors and outcomes. The system includes at least one processor and a computer readable medium coupled to the at least one processor. The computer readable medium includes instructions which when executed cause the processor to identify two or more factors that are jointly associated with one or more outcomes or factors from the data, and, analyze each of the two or more factors to determine at least one cooperative interaction among the factors with respect to an outcome or factor. The factors can be a module of factors. The module of factors can include at least one sub-module of factors. The cooperative interaction can include a structure of interactions, described by a logic function.

The two or more factors can be two or more genes, the data can include continuous gene expression data including expression levels, and the outcomes can be the presence or absence of a disease. The genes can be a module of genes. The module of genes can include at least one sub-module of genes. The module of genes can be a smallest module of genes with joint expression levels that can be used for a prediction of the presence of disease.

DETAILED DESCRIPTION

Figure 1:
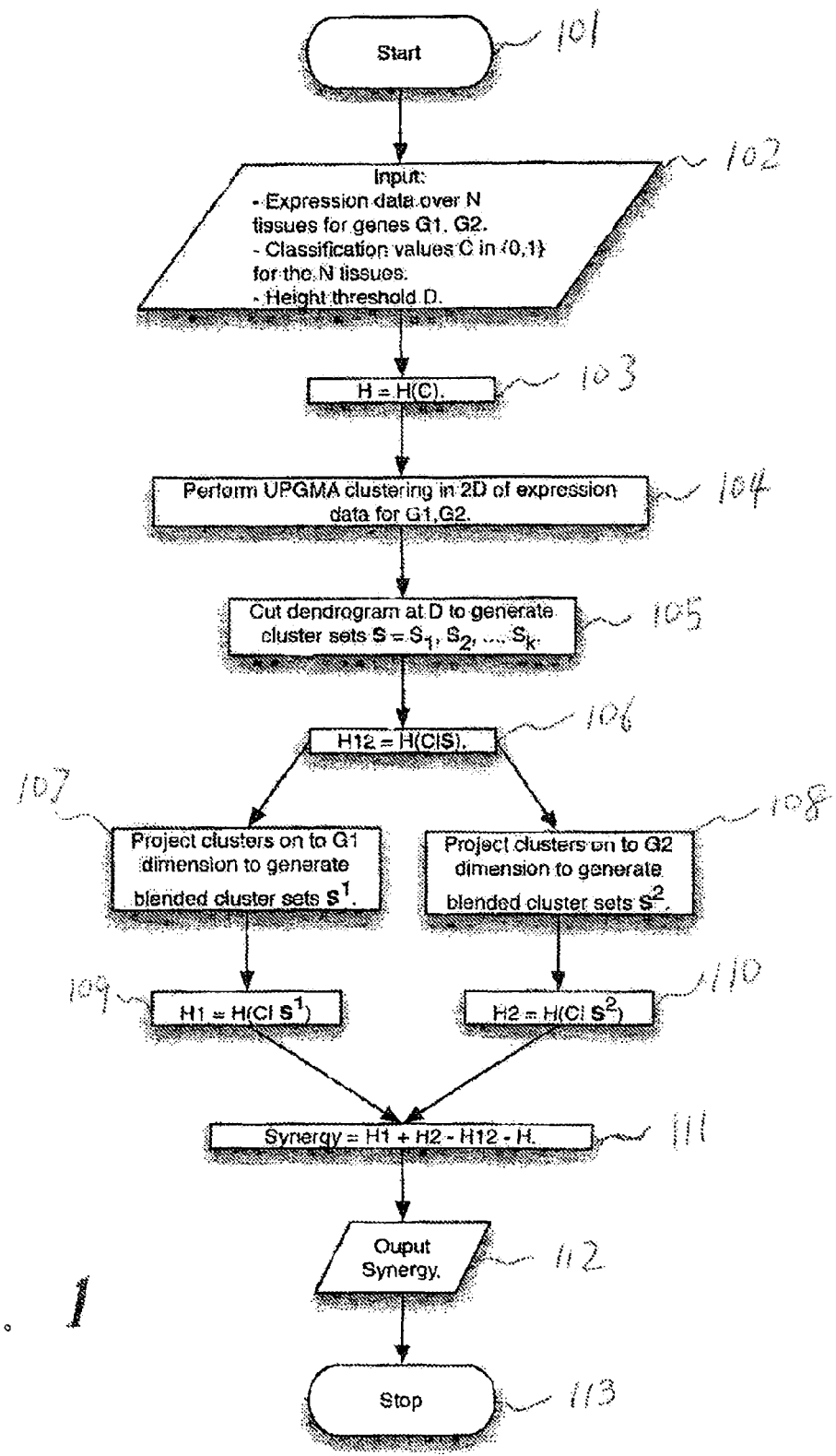
FIG. 1 is a process diagram according to some embodiments of the disclosed subject matter.

According to some aspects of the disclosed subject matter, a method for selecting factors from a data set of continuous measurements is provided. The method includes identifying factors cooperatively associated with an outcome from a continuous data set for two or more factors, and analyzing each of the factors or modules of factors to determine cooperative or synergistic interactions among the factors or outcomes with respect to the outcome. The data set can be a set of continuous measurements that includes values of the factors and the outcomes.

One application of the disclosed subject matter is where the factors are genes and the inference of the cooperative relationship or synergy among multiple interacting genes is desired. Although the following will describe disease data, it can be more generally applicable to other data sets.

Other applicable data sets include other biological data such as how cells are influenced by stimuli jointly, biomarkers, spliced isoforms, and protein expression or post-translation modification data, financial data, internet traffic data, scheduling data for industries, marketing data, and manufacturing data, for example. Table 1, below, illustrates other data sets relevant to various objectives, including factors and outcomes, to which the disclosed subject matter can also be applied. The factors can be of mixed nature, for example continuous gene expression data, combined with continuous or binary imaging biomarker data combined with binary SNP data.

TABLE 1

| Objective | Factors | Outcomes |
|---|---|---|
| Disease pathway identification | Gene expression | Disease |
| Synaptic specificity factors | Gene expression | Neural synapses |
| Disease susceptibility of specific genotypes | Single Nucleotide Polymorphisms (SNPs) | Disease |
| Genotypic basis for gene expression profiles | SNPs | Gene expression |
| Gene regulation factors | Gene expression | Gene expression |
| Gene expression association with individual SNPs | Gene expression | SNP |
| Pharmacogenomics | SNPs | Drug resistance |
| Drug side-effect modeling | SNPs | Side effect of drug |
| Biomarkers for Diagnosis, Prognosis, Treatment choice | Imaging signals, Copy number polymorphisms, Metabolite concentration level | Disease |
| Stocks/bonds/currency selling/buying price identification | Stocks/bonds/currency price time series data | Sell/Buy at given price |
| Macroeconomic models | Macroeconomic time series such as consumer index, housing market index, trade balance, etc | Federal interest rate increase/decrease |

Previously, techniques included discretization (i.e., binarization) of the data. For example, for simplification it was assumed that genes are either "on" or "off," using thresholds to binarize expression values inferred from microarrays. However, binarization of expression data imposes a constraint that limits the utility of these techniques. For example, information can be lost by not accounting for the precise intermediate expression levels. The presently disclosed subject matter avoids this limitation by evaluating continuous expression (or other) data.

In the present disclosure, the factors can be features, elements or outcomes that are cooperatively associated with one or more factors or outcomes by their joint presence or absence. The factors are selected from a data set of continuous measurements.

The measurements can include values of factors and/or outcomes. Two or more factors that are jointly associated with one or more outcomes from the data set are identified. Each of the two or more factors are analyzed to determine at least one cooperative interaction among the factors with respect to an outcome or factor. The factors can be a module of factors, where a module includes several factors acting as an individual factor, or a sub-module of factors. The interaction can be a structure of interactions, where a structure includes several interactions involving sub-modules of factors.

The factors can include two or more genes. The data set can include continuous gene expression data including expression levels for each of the genes. The outcomes include presence or absence of a disease, and the genes can be a module of genes, preferably a smallest cooperative module of genes with joint expression levels that can be used for a prediction of the presence of a disease. The cooperative interaction can be modeled using a Boolean function, a parsimonious Boolean function, or the most parsimonious Boolean function.

As illustrated below, given the continuous expression levels of some particular genes in a number of diseased and healthy samples, the uncertainty (conditional entropy) of predicting whether a sample is affected by a disease (e.g., a cancer) is estimated. The cooperative interaction is modeled by the conditional entropy and/or synergy of the genes.

The continuous gene expression can be obtained from any source. For example, it can be obtained from publicly available database, or derived from experimental data of DNA microarray analyses of genes. The continuous gene expression data include expression levels for each of the genes.

One way to evaluate the entropy of a number of genes is through clusters of samples, each sample containing continuous expression data of at least one of the genes. For the purpose of the disclosed subject matter, given a particular set of genes, a cluster is defined as a group of samples with similar expression levels of these particular genes. Given a cluster of samples, each of which is assigned one of two possible class labels referred to by the symbol C: health (C=0) or a particular disease (C=1), the entropy of the cluster is defined in equation (1):

$$h(Q) = -Q \log_2 Q - (1-Q) \log_2 (1-Q) \quad (1)$$

where Q is the relative frequency of diseased samples in the cluster. Given a partition of the full set of samples into a number of disjoint clusters, the entropy of the partition as the average of the entropies of all clusters, weighted by the relative membership of each cluster can be defined. For example, it can be assumed that there are totally $K_0$ healthy samples and $K_1$ diseased samples the total shown in equation (2):

$$K_0 + K_1 = K \quad (2)$$

and that one of the clusters contains $N_0$ healthy samples and $N_1$ diseased samples. The relative membership of the cluster is shown in equation (3):

$$P = (N_0 + N_1)/K \quad (3)$$

and the entropy of the cluster is h(Q) where Q is calculated as in equation (4):

$$Q = N_1/(N_0 + N_1). \quad (4)$$

Therefore, the entropy of the partition is equal to the sum $\Sigma Ph(Q)$ over all clusters.

Each choice of n genes defines a partition of the samples according to a clustering algorithm applied on the expression levels of these genes in all the samples. Given such a choice of genes with expression levels denoted by the symbols $G_1, \ldots, G_n$, the conditional entropy of the class label C is equal to the entropy of the resulting partition, i.e., $H(C|G_1, \ldots, G_n) = \Sigma Ph(Q)$, and measures the average uncertainty of predicting if a sample is diseased if the cluster in which the sample is located is known. In the special case that the expression levels $G_i$ are binary so that each gene is either "off" ($G_i=0$) or "on" ($G_i=1$), then this methodology becomes identical to evaluating the same conditional entropy from the probabilistic model resulting from relative frequencies after counting the number of healthy and diseased samples in each of the $2^n$ possible expression states.

The mutual information $I(G_1, \ldots, G_n; C)$ is a nonnegative quantity measuring the information that the n genes provide about the disease and is equal to $H(C)-H(C|G_1, \ldots, G_n)$, where H(C) is equal to $h(K_1/K)$. The mutual information and conditional entropy can be further normalized by dividing by H(C) so that in the normalized form $I^*(G_1, \ldots, G_n; C) = 1 - H^*(C|G_1, \ldots, G_n)$, so that the maximum normalized possible mutual information in the values of Table 1 is equal to one.

When n=2, the synergy $Syn(G_1, G_2; C)$ measures the amount of information about the disease that is due to purely cooperative effects between $G_1$ and $G_2$, and is defined as $Syn(G_1, G_2; C) = I(G_1, G_2; C) - [I(G_1; C) + I(G_2; C)]$. The synergy can also be evaluated as $H(C|G_1) + H(C|G_2) - H(C|G_1, G_2) - H(C)$. The synergy can further be normalized by dividing by H(C). Given a choice of n genes the corresponding conditional entropy H ($=\Sigma Ph(Q)$) can be estimated from the continuous expression levels of these genes. The UPGMA clustering algorithm, well known in the art as an example of distance based clustering algorithm, can be applied in evaluating the synergy.

An exemplary process for evaluation the conditional entropy and synergy of two genes is illustrated in FIG. 1. The process starts from 101, given the input 102 of expression data over N tissues for genes $G_1$ and $G_2$, classification values for the N tissues (either 0 or 1) and the height threshold D. The conditional entropy H is assigned a value of H(C) (103). UPGMA clustering is then performed for the 2D expression data for genes $G_1$ and $G_2$ (104). The UPGMA dendrogram is cut at height D to generate cluster sets $S = S_1, S_2, \ldots, S_k$ (105). Conditional entropy $H_{12}$ is evaluated as $H(C/S)$ (106). Then the cluster S is projected on $G_1$ and $G_2$ dimension to generate blended cluster sets $S^1$ and $S^2$, respectively (107 and 108), and conditional entropy $H_1$ and $H_2$ are obtained as $H(C/S^1)$ and $H(C/S^2)$, respectively (109 and 110). The synergy of genes $G_1$ and $G_2$ is then determined as $H_1 + H_2 - H_{12} - H$ (111). The synergy is output (112) and the process ends (113).

Similarly, the UPGMA clustering method can be generalized to more than two factors in higher-dimensional spaces, straightforward to those skilled in the art.

In the UPGMA dendrogram, each horizontal line at distance D from the leaves defines a partition into clusters for which a value H can be computed. The value of H changes discontinuously with D as pairs of clusters are merged into single clusters each time the horizontal line crosses the intermediate nodes of the dendrogram by moving higher. This discontinuity is undesirable, particularly because the formula for evaluating synergy involves three independent calculations of mutual information (one for the pair of genes and two for each gene alone) thus occasionally amplifying inaccuracies due to borderline effects at the discontinuity points. Furthermore, evaluating H at a specific value of D does not account for partitioning detail that can occur within the subclusters below the horizontal line at D. To remedy these issues, a measure of the conditional entropy that averages H by integrating it from 0 up to a cut-off value D* and dividing by D* is used. The value of D* can be considered to be a "threshold of biological significance," because clusters with inter-cluster distances above D* are not merged.

Various distance measures can be employed for the constructing the UPGMA dendrograms. Preferred is the Chebyshev distance measure, a well-known measure in the art defined as the maximum distance in any single dimension. This distance allows entropy values computed over different numbers of dimensions (genes) to be included in the same formula. As dimensions are added, Chebyshev distances remain limited by the maximum distance between the expression levels of two genes and therefore the same value of D* can be used for all dimensions. From a biological viewpoint, this choice assumes that the "threshold of biological significance" in the joint gene expression space of a synergistic set of genes is the same as the threshold for individual member genes. In other words, if the joint expression of two genes is causing a phenotype exclusively as a result of their synergistic interaction, then it is sufficient for one of them to exceed the threshold of biological significance for the pair of genes to cease causing the phenotype. When using the above numerical measure of conditional entropy and the Chebyshev distance measure, the following is true: $H(C|G_1, G_2) \leq \min\{H(C|G_1), H(C|G_2)\}$. This is consistent with information-theoretic facts, as is well known in the art.

The calculation of synergy according to the previously described technique requires evaluation of several conditional entropies of an outcome based on differing number of factors. For example, the synergy of two genes $G_1$ and $G_2$ with respect to a binary phenotype C, such as the class label for a particular disease requires the evaluation of three conditional entropies: $H(C|G_1, G_2)$, $H(C|G_1)$, $H(C|G_2)$. An alternative approach (the "one-step evaluation" approach) to evaluate synergy is to evaluate only one of these terms—the one determined by the maximum number of genes, i.e., $H(C|G_1, G_2)$ in the two-gene case. This quantity is then used to estimate the other terms, i.e., $H(C|G_1)$ and $H(C|G_2)$ in the two-gene case.

Two methods can be used in this one-step evaluation approach. For example, in a two-gene example, in the first method, each sample corresponds to a point in the two-dimensional space whose two coordinates are the gene expression values of the two genes. The evaluation of $H(C|G_1, G_2)$ will result in a partitioning of the set of samples into a number, say L, of clusters $S_1, S_2, \ldots, S_L$ in the two-dimensional space. As described previously, if $P_i$ is the relative membership of cluster $S_i$ and $Q_i$ is the relative frequency of diseased samples within cluster $S_i$, then $H(C|G_1, G_2)$ will be equal to $$\sum_{i=1}^{L} P_i h(Q_i).$$

The evaluation of $H(C|G_1)$ and $H(C|G_2)$ will be based on the assumption that these L clusters correspond to L biological events, except that the relative memberships and frequencies of diseased samples within each cluster will be modified to reflect the uncertainty whenever the projections of multiple clusters in the one-dimensional space overlap. For example, the value of expression of the first gene $G_1$ in a particular sample can, by itself, indicate that the sample belongs to either of three particular clusters, because it is within the range of each of the three clusters. In that case, the "membership" of that sample to each of these three clusters will be assigned the value of ⅓. In other words, for each sample, a determination can be made as to the number of clusters to which it can belong and the membership value to each of these clusters will be uniformly distributed. The determination of whether or not a sample can belong in a cluster is made by examining if the $G_1$ expression value of the sample lies within the range determined by the minimum and maximum $G_1$ values among all samples in that cluster. The value of $H(C|G_1)$ will then be also equal to $$\sum_{i=1}^{L} P_i h(Q_i),$$

except that the values of $P_i$ and $Q_i$ will be modified to reflect the new membership values after each sample has thus been fractionally assigned to each of the L clusters.

Similarly, in the general case of evaluating the synergy of n factors with respect to a binary phenotype, one clustering can be made to estimate $H(C|G_1, G_2, \ldots, G_n)$. This will result in a partitioning of the set of samples into a number, say L, of clusters $S_1, S_2, \ldots, S_L$ in the n-dimensional space; and $H(C|G_1, G_2, \ldots, G_n)$ can be evaluated as equal to $$\sum_{i=1}^{L} P_i h(Q_i).$$

The evaluation of the conditional entropy of C conditioned on m out of the n expression values, where m<n, will similarly be made by uniformly allocating the membership of each sample to each cluster to which it could potentially belong based on the limited knowledge of the m out of the n expression values of the sample. As before, the determination of whether or not a sample can belong in a cluster is made by examining if all the m expression values of the sample lie within the corresponding m ranges determined by the minimum and maximum expression values among all samples in that cluster. The value of the conditional entropy will then again be equal to $$\sum_{i=1}^{L} P_i h(Q_i),$$

except that the values of $P_i$ and $Q_i$ will be modified to reflect the new membership values.

In the second method of the one-step evaluation approach, to estimate the entropy $H(C|G)$ for a particular gene G, cluster membership values are assigned in a non-uniform way so that the values of $P_i$ (relative membership of cluster $S_i$) remain constant, i.e., as they were before the fractional allocation. This can be done as follows:

First, define a set (e.g., Set A) which initially contains all of the samples provided. For each cluster, an initial assignment of zero is made to the number of their diseased as well as healthy samples.

Then, find a set of potential clusters of the first sample in Set A. Let K be the number of these potential clusters. All the other, if any, samples are found, each of which has the identical set of K potential clusters. All these samples are included together with the first sample in a list (e.g., List A). Let N be the number of samples in List A. Define another list (e.g., List B) of size N, indicating the actual cluster (found in the highest-dimensional space) to which each of the N samples in List A belongs. In other words, the $j^{th}$ element of List B is the actual cluster to which the $j^{th}$ element of List A belongs, where j is 1, 2, . . . , N. There are totally K clusters appearing in List B. For each of these K clusters, assign a weight W(i), i=1, 2, . . . , K, equal to the number of times cluster i appears in List B divided by N. The sum of these weights is equal to 1. Then, for each sample in List A, do the following: If the sample is diseased, add W(i) to the number of diseased samples in each of the K clusters. Otherwise, add W(i) to the number of healthy samples in each of the K clusters. This method will retain the number of samples in each cluster, because the $i^{th}$ cluster will have total membership of N times W(i), which is equal to the number of times it appears in List B. It will also retain the total number of diseased and healthy samples, because the type (disease versus health) of each sample will be distributed into K clusters with weights that add to 1.

Next, remove the samples in List A from Set A. If Set A is now not empty, identify its first sample and, based on that sample, define new List A and List B and repeat the same procedure as in the previous paragraph. When Set A is found empty, all samples of the corresponding set of potential clusters have been found. At that point, stop and evaluate the entropy of the corresponding clustering partition, which is the estimate of $H(C|G)$.

The information (e.g., conditional entropy and/or synergy) gained from the continuous expression data from multiple samples can be further used in various ways. For example, given a number of samples containing continuous expression levels of a set of genes, the conditional entropy and synergy with respect to a certain outcome (e.g., cancer) can be evaluated for one of more selected subsets of the original set of genes. One or more modules of genes (some particular subsets of the genes that produce low conditional entropy or high synergy) can be identified and can then be treated as a single factor. These modules can be used as candidates for prediction of the outcome. These modules of genes can further include sub-modules of genes which produce low conditional entropy or high synergy, which can be similarly identified by evaluating conditional entropy or synergy of the subsets of the modules of genes. The low conditional entropy can be minimum conditional entropy; the high synergy can be maximum synergy.

Alternatively, an systematic evaluation of conditional entropy or synergy can be conducted for each subset of genes out of the originally given set of genes. Module(s) or sub-module(s) of the genes can be identified that produce low conditional entropy or high synergy. Smallest cooperative module of genes can also be readily identified. The low conditional entropy can be minimum conditional entropy; the high synergy can be maximum synergy. The module(s) or sub-module(s) of the genes can be used to predict a given sample containing continuous expression data of one or more genes comprising a common subset of gene(s) shared with the module(s) or sub-module(s) of the genes. In particular, when provided with a sample where gene expression data are incomplete (e.g., gene expression levels for some relevant genes are unavailable), the module(s) or sub-module(s) of genes that comprise genes for which the continuous gene expression levels are present in the sample can be advantageously used to predict the outcome of the sample. Preferably, such module(s) or sub-module(s) include a smallest cooperative module of genes.

Figure 2:
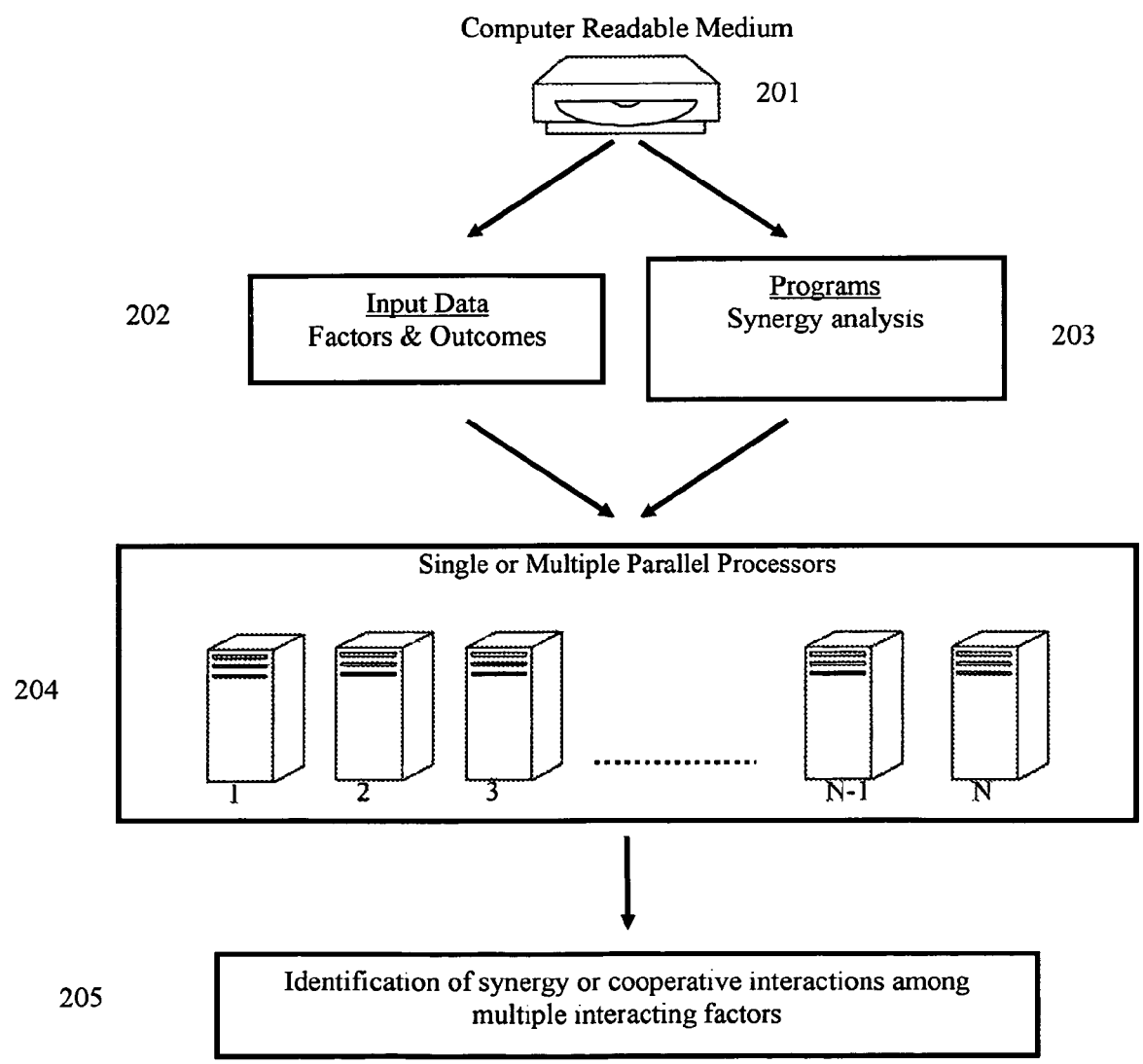
FIG. 2 is a functional diagram according to some embodiments of the disclosed subject matter.

The techniques of the disclosed subject matter can be implemented by way of off-the-shelf software such as MATLAB, JAVA, C++, or other software. Machine language or other low level languages can also be utilized. Multiple processors working in parallel can also be utilized. As illustrated in the embodiment depicted in FIG. 2, a system in accordance with the disclosed subject matter can include a processor or multiple processors 204 and a computer readable medium 201 coupled to the processor or processors 204. The computer readable medium includes data such as factors and outcomes 202 and can also include programs for synergy analysis and/or entropy analysis 203. The system leads to the identification of the synergy, synergies or cooperative interaction(s) among multiple interacting factors 205. Multiple processors 204 working in parallel can also be utilized.

In one example of the disclosed subject matter, publicly available prostate cancer expression data from 102 prostate samples are obtained, 50 of which were deemed as healthy and the remaining 52 as cancerous using RMA-normalized values (RMA normalization is one of the standard microarray gene expression normalization methods to derive expression values likely to be approximately proportional to the actual biological concentration of the mRNA produced by the genes). All genes were ranked in terms of their conditional entropy $H(C|G_i)$. The ten lowest scoring genes are shown in Table 2. These are the genes that are individually most correlated with cancer, because the same genes would equivalently have been found as highest scoring in terms of the mutual information $I(G_i; C)$. Nearly all genes in the list are well-known biomarkers of prostate cancer, such as HPN, ERG, AMACR, FOLH1, TACSTD1 and AGR2.

TABLE 2

| Rank | Symbol | Accession Number | Entropy |
|---|---|---|---|
| 1 | HPN | X07732 | 0.5151 |
| 2 | TRGV3 | M30894 | 0.6164 |
| 3 | PDLIM5 | AL049969 | 0.6503 |
| 4 | ERG | M21535 | 0.6640 |
| 5 | AMACR | AJ130733 | 0.6809 |
| 6 | NELL2 | D83018 | 0.6838 |
| 7 | CFD | M84526 | 0.6917 |
| 8 | FOLH1 | M99487 | 0.6969 |
| 9 | TACSTD1 | M93036 | 0.6973 |
| 10 | AGR2 | AF038451 | 0.7090 |

All gene pairs were then ranked in terms of their synergy $I(G_i, G_j; C)-[I(G_i; C)+I(G_j; C)]$. Genes RBP1 and EEF1B2 produce the highest synergy, indicating in combination they appear to predict prostate cancer in ways that cannot be attributed to the additive individual contributions of the genes.

Figure 3:
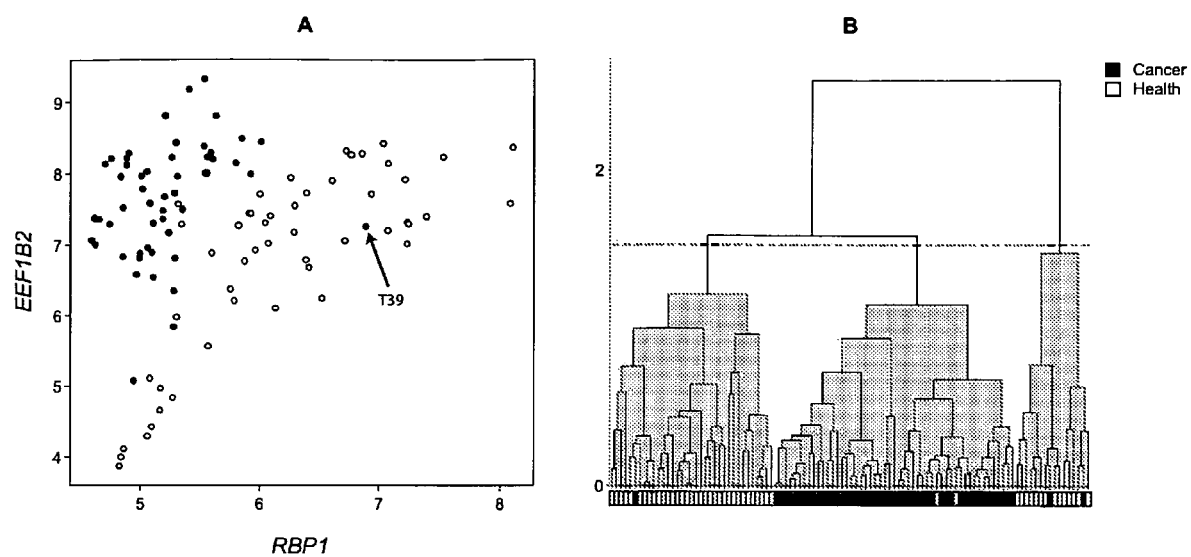
FIGS. 3(a) and (b) are graphical diagrams according to some embodiments of the disclosed subject matter.

FIG. 3(a) shows the scatter plot of gene expression data for genes RBP1 and EEF1B2. 52 cancerous samples and 50 health samples are represented by solid circles (●) and unfilled circles (○), respectively. The axes represent the expression levels of the two genes. FIG. 3(b) shows the corresponding dendrogram for the two-dimensional scatter plot in 3(a). On the horizontal axis are the genes depicted as the "leaves" of the tree, while the vertical axis measures the "distance" (dissimilarity) between clusters. The high synergy is reflected by the fact that cancer tends to occur only in the simultaneous low expression or RBP1 and high expression of EEF1B2, but not otherwise. It is noted that in FIG. 3(a), tissue T39 appears to be mislabeled, as it would be labeled as healthy using other known classification techniques.

In this example, a value of $D^*=1.5$ (the height of the shown dashed line) can be used on the RMA-normalized data. When using this averaged value of H as a figure of merit to be minimized over the choices of gene sets, there is not much sensitivity on the choice of $D^*$ in terms of the relative comparison of values of entropy or synergy associated with gene sets. For example, comparing the top 100 most synergistic pairs for $D^*=1.5$ to the top 100 pairs for $D^*=1.25$ and $D^*=1.75$, there are 83 pairs in common for $D^*=1.5$ and $D^*=1.25$, and 76 pairs in common for $D^*=1.5$ and $D^*=1.75$. Furthermore, regardless of the choice of $D^*$, this measure is still backwards compatible with the evaluation of the conditional entropy in binary expression data, in which case H is independent of $D^*$.

To further estimate the sensitivity to the choice of the parameter, the result of top 100 gene pairs using different $D^*$ values can be compared with the result using $D^*=1.5$. The results for $D^*=1.0, 1.25, 1.75$ and $2.0$ are 62%, 83%, 76% and 54%, respectively. Therefore, there is a reasonably wide range of the values of $D^*$ yielding consistent results. The biological meaning of the parameter can be the threshold of biological significance, so that each cluster is interpreted as a biological event.

The foregoing merely illustrates the principles of the disclosed subject matter. Various modifications and alterations to the described embodiments will be apparent to those skilled in the art in view of the teachings herein. For example, synergy evaluation can be based on estimating the mutual information between two continuous variables as a whole as well as in the presence and absence of disease separately. Furthermore, when the size of the set of sought biomarkers is large, one can first evaluate the pair or triplet of biomarkers that minimizes the conditional entropy, serving as a sub-module of factors, and then identify the remaining, complementary sub-module of factors so that the synergy of the two sub-modules with respect to the outcome is maximized, as described herein, in which case approximate synergy evaluation can also be conducted using recursive feature elimination.

It will thus be appreciated that those skilled in the art will be able to devise numerous techniques which, although not explicitly described herein, embody the principles of the disclosed subject matter and are thus within the spirit and scope of the disclosed subject matter.

What is claimed is:

1. A method for selecting M genes ($M \geq 2$) from continuous gene expression data, comprising:
   providing one or more samples wherein a disease is present or absent;
   providing continuous gene expression data for the one or more samples for N genes ($N \geq 2$, $N \geq M$), the continuous gene expression data comprising expression levels in the one or more samples for each of the N genes;
   evaluating a cooperative interaction, with respect to the disease, among genes in each of all the subsets of the N genes that consists of M genes, wherein evaluating the cooperative interaction comprising using a computer processor;
   ranking all the subsets each consisting of M genes based on the evaluated cooperative interaction;
   selecting one or more subsets consisting of M genes whose cooperative interaction are ranked among a predetermined number of highest ranked subsets.

2. The method of claim 1, wherein evaluating the cooperative interaction comprises evaluating conditional entropy of the M genes in each of all the subsets of the N genes that consist of M genes.

3. The method of claim 2, wherein selecting the one or more subsets consisting of M genes comprises selecting the subset having the lowest conditional entropy among all the subsets consisting of M genes.

4. The method of claim 1, wherein evaluating the cooperative interaction comprises evaluating synergy among the M genes in each of all of the subsets of the N genes.

5. The method of claim 4, wherein selecting the one or more subsets consisting of M genes comprises selecting the subset having the highest synergy among all the subsets consisting of M genes.

6. The method of claim 1, wherein the continuous gene expression data is obtained from at least one microarray of gene expression analysis.

7. The method of claim 1, wherein the M genes comprise a module of genes.

8. The method of claim 1, wherein the evaluation of the cooperative interaction is made using a distance based clustering algorithm.

9. The method of claim 8, wherein the distance based clustering algorithm is UPGMA.

10. The method of claim 1, wherein M is equal to 2.

* * * * *